(12) United States Patent
Gan

(10) Patent No.: US 11,446,218 B2
(45) Date of Patent: *Sep. 20, 2022

(54) COSMETIC COMPOSITIONS

(71) Applicant: Mary Kay Inc., Addison, TX (US)

(72) Inventor: David Gan, Southlake, TX (US)

(73) Assignee: MARY KAY INC., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/108,988

(22) Filed: Dec. 1, 2020

(65) Prior Publication Data

US 2021/0220233 A1    Jul. 22, 2021

Related U.S. Application Data

(63) Continuation of application No. 16/356,689, filed on Mar. 18, 2019, now Pat. No. 10,881,699, which is a continuation of application No. 15/799,507, filed on Oct. 31, 2017, now Pat. No. 10,272,028, which is a continuation of application No. 14/959,893, filed on Dec. 4, 2015, now Pat. No. 9,814,670.

(60) Provisional application No. 62/087,658, filed on Dec. 4, 2014.

(51) Int. Cl.

| | |
|---|---|
| A61K 8/06 | (2006.01) |
| A61K 36/185 | (2006.01) |
| A61K 36/45 | (2006.01) |
| A61K 38/06 | (2006.01) |
| A61K 38/07 | (2006.01) |
| A61K 8/42 | (2006.01) |
| A61Q 19/00 | (2006.01) |
| A61K 8/894 | (2006.01) |
| A61K 8/99 | (2017.01) |
| A61K 8/04 | (2006.01) |
| A61K 8/9789 | (2017.01) |
| A61K 8/31 | (2006.01) |
| A61K 8/34 | (2006.01) |
| A61K 8/37 | (2006.01) |
| A61K 8/41 | (2006.01) |
| A61K 8/44 | (2006.01) |
| A61K 8/49 | (2006.01) |
| A61K 8/55 | (2006.01) |
| A61K 8/58 | (2006.01) |
| A61K 8/64 | (2006.01) |
| A61K 8/81 | (2006.01) |
| A61K 8/86 | (2006.01) |
| A61K 8/891 | (2006.01) |
| A61K 8/92 | (2006.01) |
| A61Q 19/02 | (2006.01) |
| A61Q 19/08 | (2006.01) |

(52) U.S. Cl.
CPC .............. *A61K 8/062* (2013.01); *A61K 8/042* (2013.01); *A61K 8/31* (2013.01); *A61K 8/34* (2013.01); *A61K 8/342* (2013.01); *A61K 8/345* (2013.01); *A61K 8/37* (2013.01); *A61K 8/375* (2013.01); *A61K 8/41* (2013.01); *A61K 8/42* (2013.01); *A61K 8/44* (2013.01); *A61K 8/4973* (2013.01); *A61K 8/55* (2013.01); *A61K 8/585* (2013.01); *A61K 8/64* (2013.01); *A61K 8/8152* (2013.01); *A61K 8/86* (2013.01); *A61K 8/891* (2013.01); *A61K 8/894* (2013.01); *A61K 8/922* (2013.01); *A61K 8/9789* (2017.08); *A61K 8/99* (2013.01); *A61K 36/185* (2013.01); *A61K 36/45* (2013.01); *A61K 38/06* (2013.01); *A61K 38/07* (2013.01); *A61Q 19/00* (2013.01); *A61Q 19/02* (2013.01); *A61Q 19/08* (2013.01); *A61K 2800/594* (2013.01); *A61K 2800/5922* (2013.01)

(58) Field of Classification Search
CPC ................................. A61K 8/97; A61Q 19/02
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,087,445 A | 2/1992 | Haffey et al. |
| 5,100,660 A | 3/1992 | Hawe et al. |
| 6,482,446 B2 | 11/2002 | Watson |

(Continued)

FOREIGN PATENT DOCUMENTS

| | | |
|---|---|---|
| CN | 1197542 | 4/2005 |
| CN | 101690704 | 4/2010 |

(Continued)

OTHER PUBLICATIONS

Mibelle Group Biochemistry (Alpine Rose Active, http://asia.in-cosmetics.com/_novadocuments/13869, Apr. 2012) (Year: 2012).*
Schaefer (Cosmetics and Toiletries, Apr. 29, 2010, https://www.cosmeticsandtoiletries.com/cosmetic-ingredients/actives/news/21841662/alpine-rose-leaf-extract-for-environmental-protection-for-stem-cells) (Year: 2010).*
Happi (Cosmetics Go Green, May 29, 2007, https://www.happi.com/contents/view_features/2007-05-29/cosmetics-go-green/) (Year: 2007).*

(Continued)

*Primary Examiner* — Mark V Stevens
(74) *Attorney, Agent, or Firm* — Norton Rose Fulbright US LLP

(57) ABSTRACT

A method of reducing the appearance of hyperpigmented skin is disclosed. The method can include topically applying to hyperpigmented skin a composition comprising an aqueous and/or glycerin extract of *Rhododendron ferrugineum* leaf to reduce melanocyte pigmentation in the skin.

18 Claims, No Drawings

(56) References Cited

U.S. PATENT DOCUMENTS

| | | |
|---|---|---|
| 6,974,799 B2 | 12/2005 | Lintner |
| 7,160,560 B2 | 1/2007 | Pinnell |
| 7,744,932 B2 | 6/2010 | Faller et al. |
| 7,758,878 B2 | 7/2010 | Scimeca et al. |
| 7,998,493 B2 | 8/2011 | Lintner |
| 8,501,708 B2 | 8/2013 | Jagtap |
| 8,828,500 B2 | 9/2014 | Arai et al. |
| 9,125,928 B2 | 9/2015 | Kawamura et al. |
| 9,192,636 B2 | 11/2015 | Bombardelli et al. |
| 2002/0077350 A1 | 6/2002 | Babish et al. |
| 2004/0109905 A1 | 6/2004 | Bagchi |
| 2005/0074474 A1 | 4/2005 | Sako |
| 2005/0163880 A1 | 7/2005 | Pusateri et al. |
| 2006/0216254 A1* | 9/2006 | Majmudar ............. A61K 8/675 424/62 |
| 2007/0122492 A1 | 5/2007 | Behr et al. |
| 2007/0299032 A1 | 12/2007 | Ehama et al. |
| 2008/0260869 A1 | 10/2008 | Faller et al. |
| 2009/0060962 A1 | 3/2009 | Castiel et al. |
| 2009/0068160 A1 | 3/2009 | Castiel et al. |
| 2009/0143333 A1 | 6/2009 | Palefsky et al. |
| 2009/0232785 A1 | 9/2009 | Breton et al. |
| 2010/0183527 A1 | 7/2010 | Moser et al. |
| 2010/0278793 A1 | 11/2010 | Gueniche et al. |
| 2010/0305053 A1 | 12/2010 | Gueniche et al. |
| 2011/0006938 A1 | 1/2011 | Ihs et al. |
| 2011/0195102 A1 | 8/2011 | Van Den Nestt et al. |
| 2011/0300199 A1 | 12/2011 | Garcia Sanz et al. |
| 2012/0231099 A1 | 9/2012 | Castiel et al. |
| 2012/0301452 A1 | 11/2012 | Gueniche et al. |
| 2013/0101662 A1 | 4/2013 | Carreno Ra ma et al. |
| 2013/0108562 A1 | 5/2013 | Bardey et al. |
| 2014/0271525 A1 | 9/2014 | Florence |
| 2015/0342854 A1 | 12/2015 | Shibuya et al. |
| 2016/0158143 A1 | 6/2016 | Gan et al. |
| 2017/0157016 A1 | 6/2017 | Stocklin et al. |

FOREIGN PATENT DOCUMENTS

| | | |
|---|---|---|
| CN | 103534343 | 1/2014 |
| CN | 103622852 | 3/2014 |
| EP | 1159952 | 1/2009 |
| KR | 100034894 | 5/1990 |
| KR | 100581747 B1 | 5/2006 |
| KR | 100670440 | 1/2007 |
| KR | 100737101 | 7/2007 |
| KR | 100828494 | 5/2008 |
| KR | 100886494 | 3/2009 |
| KR | 100903654 | 6/2009 |
| KR | 1020090132924 | 12/2009 |
| KR | 1020100061381 | 6/2010 |
| KR | 20100092150 | 8/2010 |
| KR | 101081059 | 11/2011 |
| KR | 1020120000880 | 1/2012 |
| KR | 101125878 | 3/2012 |
| WO | WO 2008/134712 | 11/2008 |
| WO | WO 2009/046116 | 4/2009 |
| WO | WO 2011/006938 | 1/2011 |
| WO | WO 2011/116216 | 9/2011 |
| WO | WO 2012/038061 | 3/2012 |
| WO | WO 2012/107550 | 8/2012 |
| WO | WO 2015/082172 | 6/2015 |

OTHER PUBLICATIONS

Creations from Eden, pH adjusters, https://www.creationsfromeden.com/categories/raw_ingredients/ph_adjusters, copyright 2011) (Year: 2011).*

FutureDerm (What does Caprylic/Capric Triglyceride Do in Products?, Nov. 15, 2012, https://www.futurederm.com/what-does-caprylic-acidcapric-triglyceride-do-in-products/) (Year: 2012).*

"What Does Caprylic Acid/Capric Triglyceride Do in Products?" *FutureDerm*, Nov. 15, 2012, https://www.futurederm.com/what-does-caprylic-acidcapric-triglyceride-do-in-products/.

Cao et al., "Oxygen-Radical Absorbance Capacity Assay for Antioxidants", Free Radical Biol Med. 14(3): 303-311, 1993.

Creations from Eden, pH adjusters, http://www.creationsfromeden.com/categories/raw_ingredients/ph_adjusters, copyright 2011).

Database GNPD [Online] MINTEL; Apr. 1, 2014, Naruko: "Naruko am-pm RealXpert—Peptide Rejuvenating Mask", XP002754931, retrieved from www.gnpd.com Database accession No. 2337931, p. 4, line 30—p. 4, line 31.

Database GNPD [Online] MINTEL; Oct. 1, 2013, Aromatherapy Associates: "Aromatherapy Associates Rose Infinity—Moisturiser", XP002754930, retrieved from www.gnpd.com Database accession No. 2119108, p. 4, line 10—p. 4, line 14.

International Search Report and Written Opinion issued in Corresponding PCT Application No. PCT/US2018/051445, dated Jan. 9, 2019.

International Search Report and Written Opinion issued in PCT/US2015/064004, dated Mar. 31, 2016.

Li, Dongguang. *Handbook of Practical Cosmetics Technical Manual*. Chemical Industry Press, 2001, pp. 58-60 (English Translation Provided).

Loing et al., "Trifluoroacetyl-Tripeptide-2 to Target Senescence for Anti-aging Benefits" *Cosmetics & Toiletries* 2013, 9 pages.

Mibelle Group Biochemistry (Alpine Rose Active, http://asia.in-cosmetics.com/_novadocuments/13869, Apr. 2012).

Office Action issued in Chinese counterpart Application No. 201510890116.1, dated Sep. 26, 2019.

Search Report issued in Chinese counterpart Application No. 201510890116.1, dated Sep. 11, 2019.

Zheng, Shibin. *Seoul Cosmetics Shopping Book 1st edition*. China Light Industry Press, 2014, p. 38 (English Translation Provided).

Deckner, George. "Multitasking Emollients." *Prospector*, Oct. 9, 2015, https://knowledge.ulprospector.com/3202/multitasking-emollients/. Accessed Sep. 9, 2021.

Kuzminova, Juliana. "Why 24K Gold Infused Skincare is Essential for your Beauty Routine." *Frecklefarm Organics*, Dec. 8, 2016, https://www.frecklefarmorganics.com/blogs/beauty-health/why-24k-gold-infused-skincare-is-essential-for-your-beauty-routine. Accessed Sep. 9, 2021.

Maria. "Silica Skin Benefits: Heal your Skin From Within." *The Best Organic Skincare*, Mar. 13, 2016, https://thebestorganicskincare.com/silica-skin-benefits-heal-your-skin-from-within/. Accessed Sep. 9, 2021.

* cited by examiner

COSMETIC COMPOSITIONS

CROSS REFERENCE TO RELATED APPLICATIONS

This application is a continuation of U.S. patent application Ser. No. 16/356,689, filed Mar. 18, 2019, which is a continuation of U.S. patent application Ser. No. 15/799,507, filed Oct. 31, 2017 (U.S. Pat. No. 10,272,028), which is a continuation of U.S. patent application Ser. No. 14/959,893, filed Dec. 4, 2015 (U.S. Pat. No. 9,814,670), which claims priority to U.S. Provisional Application No. 62/087,658, filed Dec. 4, 2014. The contents of the above-referenced applications are incorporated into the present application by reference.

BACKGROUND OF THE INVENTION

A. Field of the Invention

Various skin formulations that are structured to in such a way to treat a wide range of skin conditions. The formulations can be used separately or in combination in a regimen format to counteract the aging process using *Rhododendron ferrugineum* (alpine rose) extract, *Oenothera biennis* (evening rose) extract, a biomimetic peptide, and a cosmetic acceptable vehicle.

B. Description of Related Art

Many factors contribute to skin aging such as the actual age of a person, the amount of exposure to environmental factors (e.g., sun light, pollution, chemicals, smoke, etc.), and how well a person has taken care of their skin. In particular, skin aging concerns two processes—intrinsic aging, which is related to the natural aging process and genetic influences, and extrinsic, or accumulated damage due to environmental factors.

Intrinsic aging process in cells and skin can be related to the function of the protein Lamin A, which is an important protein during cell division as it provides the membrane structure of the nuclease. Without functional Lamin A, the nuclear lamina creates an abnormal nuclear envelope lacking structural support. This can lead to an abnormal shaped nuclear envelope which limits cell division. A muted form of Lamin A, known as progerin, is associated with the disease progeria where patients suffer from accelerated aging, displaying signs of aging in skin as early as 2 years of age, and have a sharply shortened lifespan.

Extrinsic factors can include exposure to ultraviolet rays through sun exposure or the use of ultraviolet lamps (for example, tanning beds). Ultraviolet rays can induce oxidative stress and inflammation that leads to skin damage. The accumulation of oxidative stress through free radical formation, can damage skin proteins leading to skin aging, which includes loss of elasticity, loss of dermal proteins, lines and wrinkles, and abnormal pigmentation. Inflammation is also a characteristic of UV and environmental damage. Inflammation can occur through inflammatory cytokines such as TNFalpha, or enzymes that contribute to the inflammatory pathway such as cyclooxygenase 1, cyclooxygenase 2, and lipoxygenase. As inflammation persists, enzymes such as matrix metalloproteinase-3 (MMP3), and matrix metalloproteinase-9 (MMP9) are involved in the breakdown dermal proteins, which allows immune cells to migrate. This breakdown in dermal proteins such as laminin and collagen can lead to skin aging. When exposed to extrinsic factors such the ultra violet (UV) radiation of the sun, irritants, and pollution, the keratinocyte (outermost cell of the skin) releases signaling molecules, such as α-melanocyte-stimulating hormone (α-MSH), and inflammatory cytokines. These hormones trigger melanocytes to produce melanin. The production of melanin can result in variations in the color of the skin. For example, a person's skin can have a sallow tone or hyperpigmented spots. Conventional depigmenting agents, such as hydroquinone, corticosteroids, and kojic acid can raise several safety concerns (for example, ochronosis, atrophy, carcinogenesis, and other local or systemic side effects) with long-term exposure.

The combination of intrinsic and extrinsic factors eventually leads to visible signs of aging, and over time these signs progress through three stages—early, moderate and advanced.

The early signs of skin aging include the first stages of visible fine lines, especially around the eyes, and the beginning of uneven skin tone. Cell turnover begins to slow, and this can have a dulling effect on the complexion. Collagen and elastin—while still healthy—can start to suffer early damage, leaving skin slightly less resilient. If the matrix is left unprotected, wrinkles that are forming underneath the surface of the skin will eventually become more noticeable due to damage in the dermal layer. Eyes can occasionally look puffy, and pores appear slightly more noticeable. Typically, this occurs in an age range of about 25 to 35 years of age.

The moderate signs of skin aging include more pronounced expression lines around the eyes, the mouth and on the forehead. Underneath the eyes dark circles can become more noticeable. The skin's support structure becomes weaker as less collagen is produced, and elastin fibers begin to lose their ability to "snap" back. Skin loses vital moisture more easily, and dark spots can become more of an issue. Fine lines on the neck can become more visible, and "marionette" lines on either side of the mouth can begin to appear. More significant age spots begin to surface, eyes may look tired more often, and pores appear larger. This typically occurs in an age range of about 35 to 50 years of age.

The advanced signs of skin aging include "static" deep lines and wrinkles that are visible even when the face is at rest. The supporting structure of collagen and elastin is severely compromised and skin sagging, especially in the cheek and jawline areas, becomes evident. The neck shows signs of cumulative damage, with the skin becoming loose and marked by horizontal wrinkles called "tree rings." Dark spots become more prominent, and the eye area can show noticeable crepiness, sagging, puffiness and more pronounced dark circles in addition to a "drooping" upper eyelid. Skin loses its youthful volume and lift due to a loss of natural cushioning, and skin dryness is more pronounced as the external barrier is compromised, oil production slows and internal moisture levels drop. Cell turnover slows dramatically, and dead skin cells remain on the skin's surface which can dull the complexion and make pores more noticeable. The thickness of the skin is also impacted, and as it becomes thinner it's more easily irritated. Typically this occurs in an age range of above 50 years of age.

Current products on the market either do not effectively address ageing, and pigmentation problems, and/or they have skin irritating effects.

SUMMARY OF THE INVENTION

A solution to the problems associated with current products to counteract the effects of ageing has been discovered.

The solution resides in a combination of botanical ingredients and a biomimetic peptide that can be used to create a topical skin composition to counter oxidative damage and inflammatory damage, while increasing production of dermal proteins such as collagen and laminin, reduce pigmentation in cells and the accumulation of progerin in cells and skin.

In one aspect, there is disclosed a topical skin composition comprising *Rhododendron ferrugineum* (alpine rose) extract, *Oenothera biennis* (evening rose) extract, a biomimetic peptide, and a cosmetic acceptable vehicle. This combination can be used across all skin types (e.g., dry skin, normal skin, oily skin, and combination skin). The *Rhododendron ferrugineum* (alpine rose) can be extract of one or more leaves. Such an extract can be beneficial in countering the extrinsic factors of ageing by providing anti-oxidant properties, inhibiting breakdown of dermal proteins (for example, inhibiting cyclo-oxygenase 1 enzyme activity, cyclo-oxygenase 2 enzyme activity, and lipoxygenaze enzyme activity), reducing inflammation through reduction of TNPalpha production, and reducing pigmentation through reduction of B16 melanocyte production. The *Oenothera biennis* (evening primrose) extract can be an extract of *Oenothera biennis* (evening primrose) seeds. Such an extract can be beneficial in countering ageing effects caused by inflammation by promoting type I collagen production. An increase in type I collagen production can be beneficial in reactivating the production of matrix proteins that are crucial for skin firmness and in reducing the appearance of fine lines and wrinkles. In some aspects of the invention, the *Oenothera biennis* seed extract is an extract of an evening primrose seed that has been encapsulated in a polymer matrix. Encapsulation of the oil may allow the oil to be delivered to the deeper layers of the skin. The biomimetic peptide can be useful to counter the effects of ageing by reducing accumulation of progerin protein in fibroblasts and skin explants, and increasing collage protein expression. In some aspects of the invention, the biomimetic peptide is trifluoroacetyl tripeptide-2. The addition of tetrahexyldecyl ascorbate and adenosine may counter the effects of inflammation. Tetrahexyldecyl ascorbate and adenosine can be useful in promoting type I collagen production and inhibiting MMP3 and MMP9 enzyme activities. Promotion of type I collagen production can lessen glabellar frowns, crepiness and, thus, enhance skin smoothness. The *Rhododendron ferrugineum* extract, *Oenothera biennis* extract, and the biomimetic peptide can be mixed with the cosmetic acceptable vehicle to form an oil and water emulsion and/or a serum. The cosmetic acceptable vehicle of the present invention can include water, glycerin, crosslinked polyacrylate polymers, disodium ethylenediaminetetraacetic acid, triethanolamine, polydimethylsiloxane, and polymethyl methylacrylate. In some aspects of the invention, the cosmetic vehicle can include glycerol stearate, cetyl alcohol, cetyl phosphate, cetearyl alcohol, structuring agents, and preservatives. Addition of pentylene glycol, ethylhexyl isononoate, *Zea mays* germ oil, *butyrospermum parkii* butter, and sucrose polycottonseedate to the topical compositions of the present invention can enhance conditioning of the skin. Addition of a lysate of a fermentation product of *Bifidobacterium* (e.g., bifida ferment lysate) can enhance skin smoothness by suppressing protein-destructive enzymes (for example, MMP3 and MMP9) known to cause elasticity loss and wrinkling, as well as immune suppressive biochemicals that lower the skin's immune activity immune activity after UV exposure. In some instances, the addition of *Bifidobacterium* ferment lysate can reduce redness caused by irritation of the skin. In some aspects of the present invention, the composition is formulated as an eye cream and includes heperidin methyl chalcone, palmitoyl tetrapeptide-7. In other aspects of the present invention, addition of polysorbate 20, 1,2-hexanediol, and a copolymer of hydroxymethyl acrylate and acryloyldimethyl taurate can be used when formulating the topical composition as a serum.

In some aspects of the invention, an oil and water emulsion capable of being applied to the skin and/or the periorbital area of a person's face can include *Rhododendron ferrugineum* (alpine rose) extract, *Oenothera biennis* (evening primrose) extract, a biomimetic peptide; and a cosmetic acceptable vehicle comprising from 50% to 70% by weight of the composition of water. Such a emulsion can include 0.001 to 0.1% by weight *Rhododendron ferrugineum* (alpine rose) leaf extract, 0.001 to 1% by weight *Oenothera biennis* (evening primrose) seed extract, and 0.0001 to 0.01% by weight a biomimetic peptide. The oil and water emulsion can also include 0.1 to 2% by weight tetrahexyldecyl acorbate, and 1 to 3% by weight polydimethylsiloxane, 1 to 12% by weight of glycerin, 0.01 to 0.3% by weight crosslinked polyacrylate polymers, 0.01 to 0.2% by weight disodium EDTA, 0.01 to 1% by weight triethanolamine, and 0.01 to 1% by weight polymethyl methylacrylate. Amounts of additional ingredients include 1 to 5% by weight pentylene glycol, 1 to 5% by weight glyceryl sterate, 1 to 5% by weight ethylhexyl isononanoate, 1 to 3% by weight cetyl alcohol, 1 to 5% by weight butyrospermum parkii butter, 1 to 3% by weight cetyl phosphate, 1 to 3% by weight cetearyl alcohol, 0.01 to 1% by weight sucrose polycottonseedate, 0.01 to 1% by weight structuring agents, and 0.01 to 0.5% by weight perservatives. In embodiments when the oil and water emulsion is formulated as a skin cream, 0.1 to 2% by weight of the lysate of a fermentation product of *Bifidobacterium* can be added. In embodiments the cosmetic acceptable vehicle comprises 60 to 70% water, the emulsion can also include hesperidin methyl chalcone and palmitoyl tetrapetide-7. Such a formulation is useful as an eye cream. Methods of applying the oil and water emulsion can include applying any of the serums described throughout this Specification to a portion of a person's face and/or a portion of the periorbital region of a person's face.

In another aspect of the invention, a serum capable of being applied to the skin is provided. Such a serum includes *Rhododendron ferrugineum* (alpine rose) extract, *Oenothera biennis* (evening primrose) extract, a biomimetic peptide; and a cosmetic acceptable vehicle comprising from 50% to 70% by weight of the composition of water. Additionally, *Menyanthes trifoliata* (buckbean) extract can be used. In the serum, 0.001 to 0.1% by weight *Rhododendron ferrugineum* (alpine rose) leaf extract, 0.001 to 0.5% by weight *Oenothera biennis* (evening primrose) seed extract, 0.001 to 0.1% by weight *Menyanthes trifoliata* (buckbean) extract, and 0.0001 to 0.01% by weight a biomimetic peptide can be used. Addition of 0.1 to 2% by weight tetrahexyldecyl acorbate, and 1 to 3% by weight polydimethylsiloxane can enhance skin smoothness. The serum can also include 1 to 12% by weight of glycerin, 0.01 to 0.3% by weight crosslinked polyacrylate polymers, 0.01 to 0.2% by weight disodium ethylenediaminetetraacetic acid (EDTA), 0.01 to 1% by weight triethanolamine, and 0.01 to 1% by weight polymethyl methylacrylate. In some embodiments, the serum can include 60 to 70% water, butylene glycol, cyclopentasiloxane, hydrogenated polydecene, caprylyl glycol, squalane, panthenol, polysorbate 20, 1,2-hexanediol, and a copolymer of hydroxymethyl acrylate and acryloyldimethyl taurate. Such a serum can include 1 to 7% by weight butylene glycol, 1 to 7% by weight cyclopenta siloxane, 1 to 5% by weight hydrogenated polydecene, 0.01 to 1% by weight caprylyl glycol, 0.01 to 1% by weight squalane, 0.01 to 1% by weight panthenol, 0.01 to 1% by weight polysorbate 20, 0.01 to 0.5% by weight 1,2-hexanediol, and 0.01 to 0.5% by weight a copolymer of hydroxymethyl acrylate and acryloyldimethyl taurate. Methods of applying the serum can include applying any of the serums described throughout this Specification to a portion of a person's face.

In further aspects, the topical skin compositions described herein are comprised of a cosmetically acceptable vehicle comprising water, glyceryl stearate, cetyl phosphate, cetearyl alcohol, ceteareth-33, and carbomer. In some embodiments, the topical skin composition comprises 40 to 75 wt. % water, 4 to 10 wt. % glyceryl stearate, 0.5 to 5 wt. % cetyl phosphate, 0.5 to 5 wt. % cetearyl alcohol, 0.1 to 3 wt. % ceteareth-33, and 0.1 to 3 wt. % carbomer. In some embodiments, the composition is formulated as an oil-in-water emulsion and the cosmetically acceptable vehicle comprises 45 to 60 wt. % water and further comprises: *Butyrospermum parkii* (Shea) butter, *Zea Mays* (Corn) Germ oil, pentylene glycol, dimethicone, glycerin, triethanolamine, polymethyl methacrylate, and phenoxyethanol. In some embodiments, the topical skin composition comprises 2 to 10 wt. % *Butyrospermum parkii* (Shea) butter, 2 to 10 wt. % *Zea Mays* (Corn) Germ oil, 1 to 7 wt. % pentylene glycol, 0.5 to 5 wt. % dimethicone, 0.5 to 5 wt. % glycerin, 0.1 to 3 wt. % triethanolamine, 0.1 to 3 wt. % polymethyl methacrylate, and 0.1 to 3 wt. % phenoxyethanol.

In some embodiments of the compositions of the disclosure, the compositions further comprise an extract of *Oputia tuna*. In some embodiments, the compositions comprise 0.001 to 1 wt. % of the extract of *Oputia tuna*. In some embodiments, the *Oputia tuna* extract is a fruit extract.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. In some embodiments, the compositions of the disclosure further comprise one or more additional ingredients selected from one or more pH adjusters, preservatives, thickening agents, antioxidants, chelating agents, and emulsion stabilizers. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed are methods of inhibiting melanogenesis, melanosome transfer, and/or glycation comprising topically applying any said composition to skin in need thereof, wherein said composition inhibits melanogenesis, melanosome transfer, or glycation. In some aspects, said compositions are applied to dark spots on skin, uneven skin, or hyperpigmented skin.

Also disclosed are methods of reducing accumulation of progerin in cells and skin in a person's skin comprising applying any one of the compositions disclosed or claimed in the application to skin in need thereof.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, serum or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also disclosed herein are embodiments one to fifty. Embodiment one is a topical skin care composition comprising *Rhododendron ferrugineum* (alpine rose) extract, *Oenothera biennis* (evening primrose) extract, trifluoroacetyl tripeptide-2, and a cosmetically acceptable vehicle. Embodiment two is the topical skin care composition of embodiment one, wherein the *Rhododendron ferrugineum* (alpine rose) extract is from leaves of *Rhododendron ferrugineum* (alpine rose) and the *Oenothera biennis* (evening primrose) extract comprises oil from seeds of an *Oenothera biennis* (evening primrose), wherein the oil is encapsulated in a polymer matrix. Embodiment three is the topical skin care composition of any one of embodiments one or two, comprising 0.01 to 2 wt. % of *Rhododendron ferrugineum* (alpine rose) extract, 0.1 to 2 wt. % of *Oenothera biennis* (evening primrose) extract, and 0.0001 to 2 wt. % of trifluoroacetyl tripeptide-2. Embodiment four is the topical skin composition of any one of embodiments one to three, wherein the cosmetically acceptable vehicle comprises water, glycerin, acrylates/C10-30 alkyl acrylate crosspolymer, disodium ethylenediaminetetraacetic acid, triethanolamine, polydimethylsiloxane, and polymethyl methylacrylate. Embodiment five is the topical skin composition of embodiment 4, wherein the cosmetically acceptable vehicle comprises 50 to 75 wt. % water, 1 to 15 wt. % glycerin, 0.1 to 0.5 wt. % acrylates/C10-30 alkyl acrylate crosspolymer, 0.05 to 0.15 wt. % disodium ethylenediaminetetraacetic acid, 0.1 to 1.5 wt. % triethanolamine, 2 to 5 wt. % polydimethylsiloxane, and 0.5 to 1 wt. % polymethyl methylacrylate. Embodiment six is the topical skin composition of any one of embodiments four to five, wherein the composition is formulated as an oil-in-water emulsion and the cosmetically acceptable vehicle comprises 55 to 70 wt. % water and further comprises glyceryl stearate, pentylene glycol, ethylhexyl isononanoate, cetyl alcohol, butyrosperum parkii (shea) butter, Zea mays (cor) germ oil, cetyl phosphate, cetearyl alcohol, and ceteareth-33. Embodiment seven is the topical skin composition of embodiment six, wherein the composition further comprises 3 to 7 wt. % glyceryl stearate, 3 to 7 wt. % pentylene glycol, 2 to 5 wt. % ethylhexyl isononanoate, 2 to 5 wt. % cetyl alcohol, 1 to 3 wt. % butyrosperum parkii (shea) butter, 1 to 3 wt. % Zea mays (cor) germ oil, 1 to 3 wt. % cetyl phosphate, 1 to 3 wt. % cetearyl alcohol, and 0.5 to 1 wt. % ceteareth-33. Embodiment eight is the topical skin composition of any one of embodiments one to three, wherein the cosmetically acceptable vehicle comprises water, glyceryl stearate, cetyl phosphate, cetearyl alcohol, ceteareth-33, and carbomer. Embodiment nine is the topical skin composition of embodiment eight, wherein the cosmetically acceptable vehicle comprises 40 to 75 wt. % water, 4 to 10 wt. % glyceryl stearate, 0.5 to 5 wt. % cetyl phosphate, 0.5 to 5 wt. % cetearyl alcohol, 0.1 to 3 wt. % ceteareth-33, and 0.1 to 3 wt. % carbomer. Embodiment ten is the topical skin composition of embodiments eight or nine, wherein the composition is formulated as an oil-in-water emulsion and the cosmetically acceptable vehicle comprises 45 to 60 wt. % water and further comprises Butyrospermum parkii (Shea) butter, Zea Mays (Corn) Germ oil, pentylene glycol, dimethicone, glycerin, triethanolamine, polymethyl methacrylate, and phenoxyethanol. Embodiment eleven is the topical skin composition of embodiment ten, wherein the composition comprises 2 to 10 wt. % Butyrospermum parkii (Shea) butter, 2 to 10 wt. % Zea Mays (Corn) Germ oil, 1 to 7 wt. % pentylene glycol, 0.5 to 5 wt. % dimethicone, 0.5 to 5 wt. % glycerin, 0.1 to 3 wt. % triethanolamine, 0.1 to 3 wt. % polymethyl methacrylate, and 0.1 to 3 wt. % phenoxyethanol. Embodiment twelve is the topical skin care composition of any one of embodiments one to eleven, further comprising a lysate of a fermentation product of Bifidobacterium. Embodiment thirteen is the topical skin care composition of embodiment twelve, comprising 0.1 to 2 wt. % of the lysate of a fermentation product of Bifidobacterium. Embodiment fourteen is the topical skin care composition of any one of embodiments one to thirteen, further comprising an extract of Oputia tuna. Embodiment fifteen is the topical skin care composition of embodiment fourteen, comprising 0.001 to 1 wt. % of the extract of Oputia tuna. Embodiment sixteen is the topical skin care composition of embodiment fourteen or fifteen, wherein the Oputia tuna extract is a fruit extract. Embodiment seventeen is the topical skin care composition of any one of embodiments one to seven, further comprising heperidin methyl chalcone and palmitoyl tetrapeptide-7. Embodiment eighteen is the topical skin care composition of embodiment seventeen, wherein the combined wt. % of heperidin methyl chalcone and palmitoyl tetrapeptide-7 present in the composition is 0.01 to 2 wt. %. Embodiment nineteen is the topical skin composition of any one of embodiments four to five, wherein the composition is formulated as a serum and the cosmetically acceptable vehicle comprises 60 to 70 wt. % water and further comprises butylene glycol, cyclopentasiloxane, hydrogenated polydecene, dimethicone/vinyl dimethicone cross polymer, capryl glycol, 1,2-hexanediol, hydroxyethyl acrylate/sodium acryloyldimethyl taurate copolymer, polysorbate 20, squalene, and panthenol. Embodiment twenty is the topical skin composition of embodiment nineteen, comprising 3 to 7 wt. % butylene glycol, 3 to 7 wt. % cyclopentasiloxane, 2 to 5 wt. % hydrogenated polydecene, 1 to 3 wt. % dimethicone/vinyl dimethicone cross polymer, 0.1 to 1 wt. % capryl glycol, 0.1 to 1 wt. % 1,2-hexanediol, 0.1 to 1 wt. % hydroxyethyl acrylate/sodium acryloyldimethyl taurate copolymer, 0.1 to 1 wt. % polysorbate 20, 0.1 to 1 wt. % squalene, and 0.1 to 1 wt. % panthenol. Embodiment twenty-one is the topical skin care composition of any one of embodiments one to five and nineteen to twenty, further comprising Menyanthes trifoliata (buckbean) extract. Embodiment twenty-two is the topical skin care composition of embodiment twenty-one, wherein the Menyanthes trifoliata (buckbean) is an extract of Menyanthes trifoliata (buckbean) leaves. Embodiment twenty-three is the topical skin care composition of any one of embodiments twenty-one to twenty-two, comprising 0.001 to 2 wt. % of Menyanthes trifoliata (buckbean) extract. Embodiment twenty-four is the topical skin care composition of any one of embodiments one to twenty-three, further comprising adenosine and tetrahexyldecyl ascorbate. Embodiment twenty-five is the topical skin care composition of embodiment twenty-four, comprising 0.1 to 2 wt. % adenosine and 0.1 to 2 wt. % tetrahexyldecyl ascorbate. Embodiment twenty-six is the topical skin care composition of any one of embodiments one to twenty-five, further comprising one or more additional ingredients selected from one or more pH adjusters, preservatives, thickening agents, antioxidants, chelating agents, and emulsion stabilizers. Embodiment twenty-seven is the topical skin care composition of any one of embodiments one to twenty-six, wherein the composition is capable of inhibiting cyclo-oxygenase 1 or 2 or both enzyme activity in skin. Embodiment twenty-eight is the topical skin care composition of any one of embodiments one to twenty-seven, wherein the composition is capable of inhibiting lipoxygenase enzyme activity in skin. Embodiment twenty-nine is the topical skin care composition of any one of embodiments one to twenty-eight, wherein the composition is capable of inhibiting TNF-alpha production in skin. Embodiment thirty is the topical skin care composition of any one of embodiments one to twenty-nine, wherein the composition is capable of reducing melanocyte pigmentation in skin. Embodiment thirty-one is the topical skin care composition of any one of embodiments one to thirty, wherein the composition is capable of stimulating collagen production in skin. Embodiment thirty-two is the topical skin care composition of any one of embodiments one to thirty-one, wherein the composition is capable of reducing accumulation of progerin in skin cells or fibroblasts. Embodiment thirty-three is the topical skin care composition of any one of embodiments one to thirty-two, wherein the composition is capable of reducing MMP 3 or MMP 9, or both, activity in skin. Embodiment thirty-four is the topical skin care composition of any one of embodiments one to thirty-three, wherein the composition is capable of reducing oxidative damage caused by free radicals in skin. Embodiment thirty-five is the topical skin care composition of any one of embodiments twenty-one to twenty-three, wherein the composition is capable of stimulating laminin production in skin. Embodiment thirty-six is a method of treating skin comprising topically applying to skin in need thereof any one of the compositions of embodiments on to thirty-five to skin. Embodiment thirty-seven is the method of embodiment thirty-six, wherein the composition is applied to a fine line or wrinkle. Embodiment thirty-eight is the method of embodiment thirty-six, wherein the composition is applied to the periorbital area of a person's face. Embodiment thirty-nine is the method of embodiment thirty-eight, wherein the composition is applied to fine lines or wrinkles around the eye. Embodiment forty is the method of embodiment thirty-eight, wherein the composition is applied to under eye bags or under eye dark circles. Embodiment forty-one is the method of any one of embodiments thirty-six to forty, wherein the composition inhibits cyclo-oxygenase 1 or 2 or both enzyme activity in skin. Embodiment forty-two is the method of any one of embodiments thirty-six to forty-one, wherein the composition inhibits lipoxygenase enzyme activity in skin. Embodiment forty-three is the method of any one of embodiments thirty-six to forty-two, wherein the composition inhibits TNF-alpha production in skin. Embodiment forty-four is the method of any one of embodiments thirty-six to forty-three, wherein the composition reduces melanocyte pigmentation in skin. Embodiment forty-five is the method of any one of embodiments thirty-six to forty-four, wherein the composition stimulates collagen production in skin. Embodiment forty-six is the method of any one of embodiments thirty-six to forty-five, wherein the composition reduces accumulation of progerin in skin cells or fibroblasts. Embodiment forty-seven is the method of any one of embodiments thirty-six to forty-six, wherein the composition reduces MMP 3 or MMP 9, or both, activity in skin. Embodiment forty-eight is the method of any one of embodiments thirty-six to forty-seven, wherein the composition reduces oxidative damage caused by free radicals in skin. Embodiment forty-nine is the method of any one of embodiments thirty-six to forty-eight, wherein the composition stimulates laminin production in skin. Embodiment fifty is a method of inhibiting melanogenesis, melanosome transfer, and/or glycation comprising topically applying the composition of any one of the compositions of embodiments one to thirty-five to skin, wherein said composition inhibits melanogenesis, melanosome transfer, or glycation.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. For purposes of consisting essentially of means that inclusion of additional ingredients in the compositions do not materially affect the properties of the aforementioned combination of botanical plant extracts and cosmetic vehicle. One such instance would be the inclusion of an ingredient that has a detrimental effect (e.g., reducing the efficacy or stability) on any one of the ingredients identified said combination or on the overall effect of the composition (e.g., ability to smooth skin).

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Given the number of various products on the market today and they myriad of different skin types, a person is oftentimes at a loss to identify an appropriate product to help counteract the intrinsic and extrinsic factors that contribute to the aging process.

The cosmetic compositions and formulations of the present invention can be used to counteract the factors contributing to the aging process, maintain and improve the health of a variety of skin types. For instance, the cosmetic compositions can provide many advantages including: counteracting oxidative and inflammatory damage, increasing dermal proteins such as collagen and laminin, reducing pigmentation in cells, and reducing accumulation of progerin in cells and skin (for example, reduce accumulation of progerin protein in fibroblasts and skin explants).

These and other non-limiting aspects of the present invention are provided in the following subsections.

A. Active Ingredients

The present invention is premised on a discovery of a combination of active ingredients—*Rhododendron ferrugineum* (alpine rose) extract, *Oenothera biennis* (evening rose) extract, and a biomimetic peptide (trifluoroacetyl tripeptide-2)—that can be used to improve the skin's visual appearance, counteract the extrinsic and intrinsic effects of aging, whiten or lighten the skin's color or tone, treat hyperpigmentation and other related disorders, and even out a person's skin tone. This combination of ingredients can be used in different products (e.g., a day cream, an eye cream, and a serum) to treat various skin conditions. By way of example, a day cream can help moisturize skin and treat fine lines and wrinkles. The eye cream can help firm up skin and increase microcirculation to reduce the appearance of under eye bags while also reducing the appearance of dark circles. The serum can have a concentrated amount of these ingredients to help reduce the accumulation of proteins that can lead to skin aging.

Additional actives can be used with the combination of *Rhododendron ferrugineum* (alpine rose) extract, *Oenothera biennis* (evening rose) extract, and a biomimetic peptide (trifluoroacetyl tripeptide-2). In one instance, for example, a cream can further include *Bifidobacterium* ferment lysate and tetrahexyldecyl ascorbate to further target fines lines and wrinkles, increase skin firmness, and brightening or lightening the appearance of skin. In another instance, an under eye cream can further include tetrahexyldecyl ascorbate, hesperidin methyl chalcone, and palmitoyl tetrapeptide-7 to further improve skin firmness and increased microcirculation around the eye to reduce puffiness and dark circles. In still another instance, a serum formulation can further include *Bifidobacterium* ferment lysate and tetrahexyldecyl ascorbate to help reduce protein accumulation in skin cells. The serum can further include *Menyanthes trifoliata* (buckbean) extract.

The compositions and formulation of the present invention can be particularly beneficial for skin that has begun to develop lines, wrinkles and/or crepiness. In addition to counteracting the aging process, the combination of ingredients hydrates and brightens the skin.

*Rhododendron ferrugineum* extract: Also known as alpine rose, *Rhododendron ferrugineum* is a flowering plant native to remote mountain areas such as the Alps and Pyrennes. *Rhododendron ferrugineum* leaf extract is commercially available from a variety of sources. The leaves and flowers are known sources of flavonoids. An exemplary source can be obtained from Mirabelle AG Biochemistry. (Buchs, Switzerland USA) under the trade names Alpine Rose Active or PhYtoCellTec™ Alp Rose. The extracted compounds can be used in the compositions/formulations of the present invention as a powder and/or solutions of water and an organic solvents (for example, water, glycerin, or combinations thereof). In some embodiments, the extract includes stem cells of alpine rose leaves. It has been discovered using in in vitro testing that this ingredient has anti-oxidant effects, inhibits cyclo-oxygenase 1 enzyme activity, cyclo-oxygenase 2 enzyme activity, lipoxygenase enzyme activity, and reduces TNFalpha production and B16 melanocyte pigmentation and can be used to reduce the production of melanin in skin cells (See, Example 1).

*Oenothera biennis* extract: Also known as evening primrose, *Oenothera biennis* is a flowering plant native to eastern and central North America. The extract from the seeds of the *Oenothera biennis* is an oil and can be used as a skin conditioner. The oil can be encapsulated in a polymeric material to assist in delivery of the oil to deep areas of tissue. The encapsulated form of the oil can be powder containing at least 23% *Oenothera biennis* seed extract. This ingredient is commercially available from a variety of sources. An exemplary source can be obtained from Tagra Biotechnologies Ltd. (Netanya, Israel) under the trade name TAGROL EP01. It has been discovered using in in vitro testing that this extract increase Type I collagen production (See, Example 1).

Biomimetic peptide: In preferred embodiments of the present invention, trifluoroacetyl tripeptide-2 is used as the biomimetic peptide. The trifluoroacetyl tripeptide-2 is derived from the pepidase inhibitor 3 or Elafin. The trifluoroacetyl tripeptide-2 has been shown to improve the overall smoothness of skin by reducing accumulation of progerin protein in fibroblasts and skin explants and increase Type I collagen production. Trifluoroacetyl tripeptide-2 is commercially available from a wide range of sources. For instance, Lucas-Meyer Cosmetics (Champlan, France) produces a glycerin, water and dextran solution of trifluoroacetyl tripeptide-2 that can be used in the context of the present invention. It has been discovered using in in vitro testing that this that this extract increase Type I collagen production. (See, Example 1).

*Bifidobacterium* ferment lysate: Also known as bifida ferment lysate is a lysate of bifidobacteria consisting of bacteria metabolism products, cytoplasm fractions and cell wall components. Bifida ferment lysate is commercially available from a wide range of sources. For example, CLR (Germany) produces solutions a bifida ferment lysate in phenoxyethanol and sodium benzoate or phenoxyethanol and parabens under the trade name Repair Complex CLR™ PF.

*Menyanthes trifoliata* extract: Also known buckbean, *Menyanthes trifoliate* is a marine flowering plant found in fens and bogs of Asia, Europe and North America. *Menyanthes trifoliate* is commercially available from a variety of sources. For example, Barnet Products Corp. (Englewood Cliffs, N.J., USA) produces a glycerin, water solution of *Menyanthes trifoliate* leaf extract under the trade name Minythis. It has been discovered using in in vitro testing that this extract increases laminin production and can improve antioxidant activity (See, Example 1).

Tetrahexyldecyl ascorbate: Also commonly known as ascorbyl tetraisopalimate is an ester derivative of Vitamin C. Tetrahexyldecyl ascorbate is commercially available from a variety of sources. For instance, Barnet Products sells the compound under the trade name BV-OSC. It has been discovered using in vitro testing that this compound increases Type I collagen production and inhibits MMP3 and MMP9 enzyme activity (See, Example 1).

Hesperidin Methyl Chalcone and *Palmitoyl tetrapetide*-7 are described in U.S. Pat. No. 7,998,493 to Lintner, which is incorporated herein by reference. The mixture is commercially available from Sederma SAS (France) and sold under the tradename Eyeliss™. The combination of Hesperidin Methyl Chalcone and Palmitoyl tetrapetide-7 are known to reduce bags and puffiness under the eyes.

Adenosine is an organic compound that includes an adenine compound attached to a ribose sugar. A representative structure of adenosine is shown in Equation (I).

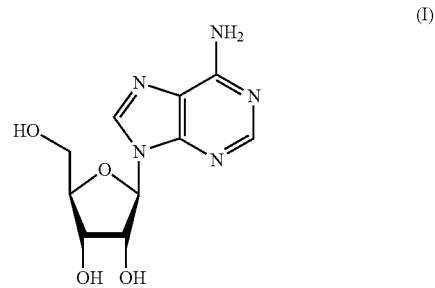

Without wishing to be bound by theory, it is believed that adenosine is an anti-inflammatory agent at the $A_{24}$ receptor. Adenosine is used in the phosphate energy cycle (i.e., ADP and ATP energy cycles). Adenosine may promote elastin and collagen production, and thus reduce skin crepiness and improve skin tone. Adenosine may also promote blood flow to the outer layers of the skin. Promotion of blood flow and enhancement of elastin and collagen production can result in a smoother skin appearance. Adenosine is commercially available from a wide range of supplies. An exemplary supplier is Xinxiang Tuoxin Biochemical Technology & Science Company Ltd. (China).

*Opuntia tuna* fruit extract: Also commonly known as prickly pear, *Opuntia tuna* is the fruit of a family of cactus native to the Americas. The extract is commercially available from a wide range of sources (see International Cosmetic Ingredient Dictionary and Handbook, 12th edition, volume 2, page 1731 (2008), which is incorporated by reference).

B. Cosmetic Vehicle

The cosmetic vehicle of the present invention has been designed to work for all skin types (e.g., oily, dry, or combination) and all age ranges. The cosmetic vehicle can be formulated as a skin cream, an eye cream, or a serum. Non-limiting examples of the cosmetic vehicle include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

In one instance, the cosmetic vehicle can include 50 to 70% water, 1 to 3% by weight polydimethylsiloxane, 1 to 12% by weight of glycerin, 0.01 to 0.3% by weight crosslinked polyacrylate polymers, 0.01 to 0.2% by weight disodium EDTA, 0.01 to 1% by weight triethanolamine, and 0.01 to 1% by weight polymethyl methylacrylate 1 to 5% by weight pentylene glycol, 1 to 5% by weight glyceryl sterate, 1 to 5% by weight ethylhexyl isononanoate, 1 to 3% by weight cetyl alcohol, 1 to 5% by weight butyrospermum parkii butter, 1 to 3% by weight cetyl phosphate, 1 to 3% by weight cetearyl alcohol, 0.01 to 1% by weight sucrose polycottonseedate, 0.01 to 1% by weight structuring agents, and 0.01 to 0.5% by weight perservatives. In another instance, the cosmetic vehicle can include 60 to 70% water, 1 to 12% by weight of glycerin, 0.01 to 0.3% by weight crosslinked polyacrylate polymers, 0.01 to 0.2% by weight disodium ethylenediaminetetraacetic acid (EDTA), 0.01 to 1% by weight triethanolamine, and 0.01 to 1% by weight polymethyl methylacrylate. In some embodiments, the serum can include 60 to 70% water, butylene glycol, cyclopentasiloxane, hydrogenated polydecene, caprylyl glycol, squalane, panthenol, polysorbate 20, 1,2-hexanediol, and a copolymer of hydroxymethyl acrylate and acryloyldimethyl taurate, 1 to 7% by weight butylene glycol, 1 to 7% by weight cyclopenta siloxane, 1 to 5% by weight hydrogenated polydecene, 0.01 to 1% by weight caprylyl glycol, 0.01 to 1% by weight squalane, 0.01 to 1% by weight panthenol, 0.01 to 1% by weight polysorbate 20, 0.01 to 0.5% by weight 1,2-hexanediol, and 0.01 to 0.5% by weight a copolymer of hydroxymethyl acrylate and acryloyldimethyl taurate.

C. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

D. Additional Ingredients

In addition to the active ingredients and cosmetic vehicles, the compositions can also include additional ingredients such as cosmetic ingredients and other pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturizing mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. *Aloe vera*, chamomile, cucumber extract, *Ginkgo biloba*, *ginseng*, and rosemary), anti-microbial agents, antioxidants (e.g., BHT and tocopherol), chelating agents (e.g., disodium EDTA and tetrasodium EDTA), preservatives (e.g., methylparaben, propylparaben, iodopropynyl butylcarbamate, and sodium benzoate), pH adjusters (e.g., sodium hydroxide, acetic acid, lactic acid, and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, and mannitol), exfoliants, emulsifier stabilizers (e.g., hydroxypropyl cyclodextrin), waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis-diethylamino hydroxybenzoyl benzoate, bis benzoxazoylphenyl ethylhexylimino-triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl-4-methoxycinnamate. Non-limiting examples of physical sun blocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (prunus armeniaca) kernel oil, arginine, arginine aspartate, arnica montana extract, aspartic acid, avocado (persea gratissima) oil, barrier sphingolipids, butyl alcohol, beeswax, behenyl alcohol, beta-sitosterol, birch (betula alba) bark extract, borage (Borago officinalis) extract, butcherbroom (ruscus aculeatus) extract, butylene glycol, *Calendula officinalis extract, Calendula officinalis* oil, candelilla (*Euphorbia cerifera*) wax, canola oil, caprylic/capric triglyceride, cardamom (elettaria cardamomum) oil, carnauba (*Copernicia cerifera*) wax, carrot (*Daucus carota* sativa) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*)oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica* linomum) oil, linoleic acid, linolenic acid, macadamia ternifolia nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium* dulcis) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus* dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (cananga odorata) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture thereof.

Non-limiting examples of additional thickening agents that can be used in the context of the present invention include carboxylic acid polymers, cross-linked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid cross-linked with allyl ethers of sucrose or pentaerythritol (e.g., Carbopol™ 900 series from B. F. Goodrich).

Non-limiting examples of cross-linked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, iso-paraffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid and salts thereof, thimerosal, potassium sorbate, or combinations thereof 2. Pharmaceutical Ingredients Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antip soriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including difluoromethylonithine (DFMO) and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

E. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Efficacy of Active Ingredients

In vitro bioassays described below were used to determine the efficacy of *Rhododendron ferrugineum* leaf (alpine rose) extract, *Oenothera biennis* seed extract (evening primrose) extract, trifluoroacetyl tripeptide-2, tetrahexyldecyl ascorbate, and *Menyanthes trifoliate* leaf extract.

Antioxidant (AO) assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®.+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation was compared with that of Trolox, a water-soluble tocopherol analogue, and was quantified as molar Trolox equivalents. Anti-Oxidant capacity kit #709001 from Cayman Chemical (Ann Arbor, Mich. USA) was used as an in vitro bioassay to measure the total anti-oxidant capacity of each of any one of the active ingredients, combination of ingredients, or compositions having said combinations disclosed in the specification. The protocol was followed according to manufacturer recommendations. The assay relied on antioxidants in the sample to inhibit the oxidation of ABTS® (2,2'-azino-di-[3-ethylbenzthiazoline sulphonate]) to ABTS®.+ by metmyoglobin. The capacity of the antioxidants in the sample to prevent ABTS oxidation was compared with that Trolox, a water-soluble tocopherol analogue, and was quantified as a molar Trolox equivalent. Using this assay, *Rhododendron ferrugineum* leaf extract demonstrated an antioxidant activity of 98% and *Menyanthes trifoliate* leaf extract demonstrated anti-oxidant activity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) was used to analyze the effects of *Rhododendron*

*ferrugineum* extract or other active ingredients, any one of the combination of ingredients, or compositions having said combinations disclosed in the specification on the activity of purified cyclooygnase enzyme (COX-1 or COX-2). According to manufacturer instructions, purified enzyme, heme and test extracts was mixed in assay buffer and incubated with shaking for 15 min at room temperature. Following incubation, arachidonic acid and colorimetric substrate was added to initiate the reaction. Color progression was evaluated by colorimetric plate reading at 590 nm. The percent inhibition of COX-1 or COX-2 activity was calculated compared to non-treated controls to determine the ability of test extracts to inhibit the activity of purified enzyme. Using this assay it was determined that *Rhododendron ferrugineum* leaf extract inhibited COX-1 activity by 68% and COX-2 activity by 69%.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) was used to determine the ability of *Rhododendron ferrugineum* extract or any of the active ingredients, any one of the combination of ingredients, or compositions having said combinations disclosed in the specification to inhibit enzyme activity. Purified 15-lipoxygenase and test ingredients was mixed in assay buffer and incubated with shaking for 10 min at room temperature. Following incubation, arachidonic acid was added to initiate the reaction and mixtures incubated for an additional 10 min at room temperature. Colorimetric substrate was added to terminate catalysis and color progression was evaluated by fluorescence plate reading at 490 nm. The percent inhibition of lipoxyganse activity was calculated compared to non-treated controls to determine the ability of each of the active ingredients, any one of the combination of ingredients, or compositions having said combinations disclosed in the specification to inhibit the activity of purified enzyme. Using this assay it was determined that *Rhododendron ferrugineum* leaf extract inhibited lipoxygenaze enzyme activity by 45%.

Tumor Necrosis Factor Alpha (TNF-$\alpha$) Assay: The prototype ligand of the TNF superfamily, TNF-$\alpha$, is a pleiotropic cytokine that plays a central role in inflammation. Increase in its expression is associated with an up regulation in pro-inflammatory activity. This bioassay was used to analyze the effect of *Rhododendron ferrugineum* leaf extract on the production of TNF-$\alpha$ by human epidermal keratinocytes. The endpoint of this assay was determined using a spectrophotometric measurement that reflects the presence of TNF-$\alpha$ and cellular viability. The assay employs the quantitative sandwich enzyme immunoassay technique whereby a monoclonal antibody specific for TNF-$\alpha$ was pre-coated onto a microplate. Standards and samples can be pipetted into the wells and any TNF-$\alpha$ present was bound by the immobilized antibody. After washing away any unbound substances, an enzyme-linked polyclonal antibody specific for TNF-$\alpha$ was added to the wells. Following a wash to remove any unbound antibody-enzyme reagent, a substrate solution was added to the wells and color develops in proportion to the amount of TNF-$\alpha$ bound in the initial step using a microplate reader for detection at 450 nm. The color development was stopped and the intensity of the color was measured. Subconfluent normal human adult keratinocytes (Cascade Biologics) cultivated in EpiLife standard growth medium (Cascade Biologics) at 37° C. in 5% $CO_2$, was treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-$\alpha$ secretion which peaks at 6 hours after treatment. Following incubation, cell culture medium was collected and the amount of TNF-a secretion quantified using a sandwich enzyme linked immuno-sorbant assay (ELISA) from R&D Systems (#DTA00C). Using this assay it was determined that *Rhododendron ferrugineum* leaf extract inhibited TNF-$\alpha$ production by 66%.

B16 Melanogenesis Assay: B16 Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay was determined using a spectrophotometric measurement of melanin production and cellular viability. B16-F1 melanocytes, was cultivated in standard DMEM growth medium with 10% fetal bovine serum (Mediatech) at 37° C. in 10% $CO_2$ and then treated with *Rhododendron ferrugineum* extract or any one of the active ingredients, combination of ingredients, or compositions having said combinations disclosed in the specification for 6 days. Following incubation, melanin secretion was measured by absorbance at 405 nm and cellular viability was quantified. Using this assay it was determined that *Rhododendron ferrugineum* leaf extract reduced B16 melanogenesis by 38%.

Collagen Stimulation Assay: Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide was been pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color develops in proportion to the amount of procollagen peptide bound in the initial step using a microplate reader for detection at 450 nm. The color development was stopped and the intensity of the color was measured. Subconfluent normal human adult epidermal fibroblasts (Cascade Biologics) cultivated in standard DMEM growth medium with 10% fetal bovine serum (Mediatech) at 37° C. in 10% $CO_2$, was treated with the compounds listed in Table 1 or each of the combination of ingredients or compositions having said combinations disclosed in the specification for 3 days. Following incubation, cell culture medium was collected and the amount of pro-collagen peptide secretion quantified using a sandwich enzyme linked immuno-sorbant assay (ELISA) from Takara (#MK101).

TABLE 1

| Ingredient | % Increase of Type I Collagen Production |
| --- | --- |
| Oenothera Biennis Seed Extract | 117 |
| Trifluoroacetyl tripeptide-2 | 23 |
| Tetrahexyldecyl ascorbate | 50 |

Matrix Metalloproteinase Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7). The active ingredients, any one of the combination of ingredients, or compositions having said combinations disclosed in the specification can be assayed. The assay results for tetrahexyldecyl ascorbate and Menyanthes trifoliate leaf extract are listed in Table 2.

TABLE 2

| Ingredient | % MMP3 Activity | % MMP9 Activity | % Laminin Increase |
| --- | --- | --- | --- |
| Tetrahexyldecyl ascorbate | 38 | 11 | — |
| Menyanthes trifoliate leaf extract | 23 | — | 400 |

Example 2

Delivery Vehicle for Active Ingredients

Various combinations of the active ingredients discussed above in Example 1 were found to be stable and effective in various delivery vehicles described in Tables 3-5. Further, these vehicles can be combined with additional ingredients to prepare an end-product such as the creams and serums identified in Tables 6-9 in Example 3.

TABLE 3

| Ingredients | % Concentration (by weight) |
| --- | --- |
| water | 58 |
| glycerin | 11.9 |
| polydimethylsiloxane | 2.7 |
| triethanolamine | 0.9 |
| polymethyl methylacrylate | 0.72 |

TABLE 3-continued

| Ingredients | % Concentration (by weight) |
| --- | --- |
| acrylates/C10-30 alkyl acrylate crosspolymer | 0.1 |
| disodium ethylenediaminetetraacetic acid | 0.1 |
| active ingredients* | up to 5 |
| excipients** | q.s. |

*Rhododendron ferrugineum leaf (alpine rose) extract, Oenothera biennis seed extract (evening primrose) extract, trifluoroacetyl tripeptide-2, tetrahexyldecyl ascorbate, and Menyanthes trifoliate leaf extract.
**structuring agents, fragrances, and preservatives. Alternatively, the amount of water can be varied upwards by removing the excipients.

TABLE 4

| Ingredients | % Concentration (by weight) |
| --- | --- |
| water | 67 |
| glycerin | 2.1 |
| polydimethylsiloxane | 2.8 |
| triethanolamine | 0.9 |
| polymethyl methylacrylate | 0.72 |
| acrylates/C10-30 alkyl acrylate crosspolymer | 0.1 |
| disodium ethylenediaminetetraacetic acid | 0.1 |
| active ingredients* | up to 5 |
| excipients** | q.s. |

*Rhododendron ferrugineum leaf (alpine rose) extract, Oenothera biennis seed extract (evening primrose) extract, trifluoroacetyl tripeptide-2, tetrahexyldecyl ascorbate, and Menyanthes trifoliate leaf extract.
**structuring agents, fragrances, and preservatives. Alternatively, the amount of water can be varied upwards by removing the excipients.

TABLE 5

| Ingredients | % Concentration (by weight) |
| --- | --- |
| water | 66 |
| glycerin | 10.9 |
| polydimethylsiloxane | 3.5 |
| triethanolamine | 0.25 |
| polymethyl methylacrylate | 0.73 |
| acrylates/C10-30 alkyl acrylate crosspolymer | 0.3 |
| disodium ethylenediaminetetraacetic acid | 0.1 |
| active ingredients* | up to 5 |
| excipients** | q.s. |

*Rhododendron ferrugineum leaf (alpine rose) extract, Oenothera biennis seed extract (evening primrose) extract, trifluoroacetyl tripeptide-2, tetrahexyldecyl ascorbate, and Menyanthes trifoliate leaf extract.
**structuring agents, fragrances, and preservatives. Alternatively, the amount of water can be varied upwards by removing the excipients.

Example 3

Product Formulations

The formulations in Tables 6-8 incorporate various combinations of the actives in Example 1 and the delivery vehicles in Example 2. Each of these formulations are oil-in-water emulsions. Table 6 is designed as a skin cream. Table 7 is designed as an eye cream for application around the periorbital area of a person (e.g., under the eye bags and circles and on "crows feet"). Table 8 is designed as a serum.

TABLE 6*

| Ingredient | % Concentration (by weight) |
| --- | --- |
| Water | 58 |
| Glycerin | 11.92 |
| Glyceryl Sterate | 4.30 |
| Pentylene Glycol | 4.28 |

TABLE 6*-continued

| Ingredient | % Concentration (by weight) |
|---|---|
| Ethylhhexyl Isononanate | 3.15 |
| Dimethicone | 2.70 |
| Cetyl Alcohol | 2.70 |
| *Butyrospermum Parkii* (Shea) Butter | 2.20 |
| *Zea Mays* (corn) Germ Oil | 1.94 |
| Cetyl Phosphate | 1.58 |
| Cetearyl Alcohol | 1.44 |
| Tetrahexyldecyl Ascorbate | 1.00 |
| Bifida Ferment Lysate | 0.99 |
| Triethonolamine | 0.90 |
| Polymethyl Methacrylate | 0.72 |
| Ceteareth-33 | 0.68 |
| *Oenothera Biennis* (evening primrose) Extract | 0.25 |
| Methylparaben | 0.20 |
| Acrylate cross-linked polymer C10-C30 | 0.25 |
| Fragrance | 0.1 |
| Propylparaben | 0.1 |
| Disodium EDTA | 0.1 |
| *Rhododendron Ferrugineum* extract | 0.02 |
| Adenosine | 0.04 |
| Trifuoroacetyl Tripeptide-2 | 0.004 |
| *Opuntia Tuna* Fruit Extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20 to 25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 50% w/w, and preferably between 50 to 75% w/w.

TABLE 7*

| Ingredient | % Concentration (by weight) |
|---|---|
| Water | 68 |
| Glyceryl Sterate | 4.28 |
| Pentylene Glycol | 4.00 |
| Ethylhhexyl Isononanate | 3.00 |
| Dimethicone | 2.80 |
| Cetyl Alcohol | 2.70 |
| *Butyrospermum Parkii* (Shea) Butter | 2.60 |
| *Zea Mays* (corn) Germ Oil | 2.425 |
| Glycerin | 2.10 |
| Cetyl Phosphate | 1.58 |
| Cetearyl Alcohol | 1.44 |
| Tetrahexyldecyl Ascorbate | 1.00 |
| Triethonolamine | 0.90 |
| Polymethyl Methacrylate | 0.72 |
| Ceteareth-33 | 0.68 |
| *Oenothera Biennis* (evening primrose) Extract | 0.25 |
| Methylparaben | 0.20 |
| Acrylate cross-linked polymer C10-C30 | 0.20 |
| BHT | 0.10 |
| Propylparaben | 0.10 |
| Disodium EDTA | 0.10 |
| Hesperidin Methyl Chalcone | 0.05 |
| Adenosine | 0.04 |
| *Rhododendron Ferrugineum* extract | 0.02 |
| Trifuoroacetyl Tripeptide-2 | 0.004 |
| Palmitoyl Tetrapeptide-7 | 0.0003 |
| *Opuntia Tuna* Fruit Extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20 to 25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 50% w/w, and preferably between 50 to 75% w/w.

TABLE 8*

| Ingredient | % Concentration (by weight) |
|---|---|
| Water | 66 |
| Glycerin | 10.9 |
| Butylene Glycol | 5.00 |
| Cyclopentasiloxane | 4.96 |
| Dimethicone | 3.50 |
| Hydrogenated Polydecene | 3.00 |
| Cross-linked Polymer of Dimethicone/vinyl Dimeth Dimethicone | 1.24 |
| Tetrahexyldecyl Acorbate | 1.00 |
| Polymethyl Methacrylate | 0.73 |
| Caprylyl Glycol | 0.53 |
| 1,2-Hexanediol | 0.47 |
| Hydroxyethyl Acrylate/Sodium Acryloyldimethyl Taurate Copolymers | 0.30 |
| Polysorbate 20 | 0.30 |
| Cross-linked Copolymer of Acrylates C10-C30 | 0.30 |
| Squalane | 0.255 |
| *Oenothera Biennis* (evening primrose) Extract | 0.25 |
| Triethanolamine | 0.25 |
| Panthenol | 0.20 |
| Disodium EDTA | 0.10 |
| Xanthum gum | 0.10 |
| Adenosine | 0.04 |
| *Rhododendron Ferrugineum* extract | 0.02 |
| *Menyanthes Trifoliata* Leaf Extract | 0.01 |
| Trifuoroacetyl Tripeptide-2 | 0.004 |
| *Opuntia Tuna* Fruit Extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20 to 25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 50% w/w, and preferably between 50 to 75% w/w.

TABLE 9*

| Ingredient | % Concentration (by weight) |
|---|---|
| Water | 50 |
| Glyceryl Sterate | 7 |
| *Butyrospermum Parkii* (Shea) Butter | 6 |
| *Zea Mays* (corn) Germ Oil | 5 |
| Pentylene Glycol | 4 |
| Dimethicone | 2 |
| Cetyl Phosphate | 2 |
| Glycerin | 2 |
| Cetearyl Alcohol | 1.5 |
| Triethonolamine | 1.5 |
| Tetrahexyldecyl Ascorbate | 1 |
| Bifida ferment lysate | 1 |
| Ceteareth-33 | 0.5 |
| Polymethyl Methacrylate | 0.5 |
| Phenoxyethanol | 0.5 |
| Carbomer | 0.5 |
| *Oenothera Biennis* (evening primrose) Seed Extract | 0.25 |
| Methylparaben | 0.2 |
| BHT | 0.2 |
| Disodium EDTA | 0.1 |
| Propylparaben | 0.1 |
| Hydroxypropyl Cyclodextrin | 0.1 |
| Adenosine | 0.05 |
| *Rhododendron Ferrugineum* extract | 0.02 |
| Iodopropynyl butylcarbamate | 0.01 |
| Sodium benzoate | 0.003 |
| Acetic acid | 0.002 |
| Dextran | 0.001 |
| Lactic acid | 0.001 |
| Trifuoroacetyl Tripeptide-2 | 0.0004 |

TABLE 9*-continued

| Ingredient | % Concentration (by weight) |
| --- | --- |
| Citric Acid | 0.0001 |
| *Opuntia Tuna* Fruit Extract (optional) | 0.05 |
| Excipients** | q.s. |

*Formulation can be prepared by mixing the ingredients in a beaker under heat 70-75° C. until homogenous. Subsequently, the formulation can be cooled to standing room temperature (20 to 25° C.). Further, and if desired, additional ingredients can be added, for example, to modify the rheological properties of the composition.
**Excipients were added to modify the rheological properties of the composition. Alternatively, the amount of water can be varied so long as the amount of water in the composition is at least 50% w/w, and preferably between 50 to 75% w/w.

Example 4

Other Assays

Other assays that can be used to evaluate the active ingredients, any one of the combination of ingredients, or compositions having said combinations disclosed in the specification can be assayed are described below.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Elastase Assay: EnzChek® Elastase Assay (Kit # E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method of reducing the appearance of hyperpigmented skin, the method comprising topically applying to hyperpigmented skin a composition comprising an effective amount of an aqueous and/or glycerin extract of *Rhododendron ferrugineum* leaf to reduce melanocyte pigmentation in the skin, wherein the hyperpigmented skin is a dark spot on the skin associated with aging or skin having uneven skin tone.

2. The method of claim 1 wherein the hyperpigmented skin is a dark spot on the skin associated with aging.

3. The method of claim 1, wherein the hyperpigmented skin is skin having an uneven skin tone.

4. The method of claim 1, wherein the composition is an emulsion.

5. The method of claim 4, wherein the emulsion is an oil-in-water emulsion.

6. The method of claim 1, wherein the composition is a cream or lotion.

7. The method of claim 1, wherein the composition is an aqueous solution or a gel.

8. The method of claim 1, wherein the composition comprises 0.001 wt. % to 5 wt. % of the extract of *Rhododendron ferrugineum* leaf.

9. The method of claim 1, wherein the composition comprises 0.001 wt. % to 2 wt. % of the extract of *Rhododendron ferrugineum* leaf.

10. The method of claim 1, wherein the composition comprises 0.001 wt. % to 0.5 wt. % of the extract of *Rhododendron ferrugineum* leaf.

11. The method of claim 1, wherein the composition consists of the extract of *Rhododendron ferrugineum* leaf, water, and glycerin.

12. The method of claim 1, wherein the composition consists of the extract of *Rhododendron ferrugineum* leaf, a polysaccharide, lecithin, and water.

13. The method of claim 1, wherein the composition further comprises a pH adjuster.

14. The method of claim 13, wherein the composition consists of the extract of *Rhododendron ferrugineum* leaf, water, glycerin, and the pH adjuster.

15. The method of claim 1, wherein the composition consists of the extract of *Rhododendron ferrugineum* leaf and caprylic/capric triglyceride.

16. The method of claim 1, wherein the extract of *Rhododendron ferrugineum* leaf is an aqueous extract.

17. The method of claim 1, wherein the extract of *Rhododendron ferrugineum* leaf is an aqueous and glycerin extract.

18. The method of claim 1, wherein the extract comprises stem cells from the *Rhododendron ferrugineum* leaf.

\* \* \* \* \*